US012059350B2

(12) United States Patent
Bruner

(10) Patent No.: US 12,059,350 B2
(45) Date of Patent: Aug. 13, 2024

(54) SPRING LOADED SELF LOCKING REVERSIBLE ANCHOR

(71) Applicant: Boston Scientific Scimed, Inc., Maple Grove, MN (US)

(72) Inventor: Kenny D. Bruner, Windsor, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 902 days.

(21) Appl. No.: 17/015,268

(22) Filed: Sep. 9, 2020

(65) Prior Publication Data

US 2021/0068955 A1 Mar. 11, 2021

Related U.S. Application Data

(60) Provisional application No. 62/898,240, filed on Sep. 10, 2019.

(51) Int. Cl.
*A61F 2/24* (2006.01)
(52) U.S. Cl.
CPC .......... *A61F 2/2445* (2013.01); *A61F 2/2466* (2013.01); *A61F 2220/0016* (2013.01)
(58) Field of Classification Search
CPC ........ A61F 2/24; A61F 2/2445; A61F 2/2466; A61F 2/2487; A61F 2/2409
See application file for complete search history.

(56) References Cited

U.S. PATENT DOCUMENTS

| 9,180,005 | B1 | 11/2015 | Lashinski et al. |
| 9,610,156 | B2 | 4/2017 | Lashinski |
| 9,788,948 | B2 | 10/2017 | Gilmore et al. |
| 10,335,275 | B2 | 7/2019 | Lashinski et al. |
| 10,555,813 | B2 | 2/2020 | Lashinski et al. |
| 2008/0082130 | A1 | 4/2008 | Ward |
| 2018/0228610 | A1* | 8/2018 | Lashinski ............. A61F 2/2466 |

OTHER PUBLICATIONS

International Search Report and Written Opinion for the International Patent Application No. PCT/US2020/049820, mailed Nov. 26, 2020, 14 pages.

* cited by examiner

*Primary Examiner* — William H Matthews
(74) *Attorney, Agent, or Firm* — Seager, Tufte & Wickhem, LLP

(57) ABSTRACT

A spring loaded, self-locking anchoring assembly converts a drive force, administered to an anchor of the anchoring assembly, to one or both of an axial translation force or a compression force. The axial translation force may be used to drive the anchor into tissue, while the compression force may be used to further draw together anchor components and tissue, and/or to lock together anchor components, to improve anchor efficacy in the presence of anatomical variations.

6 Claims, 8 Drawing Sheets

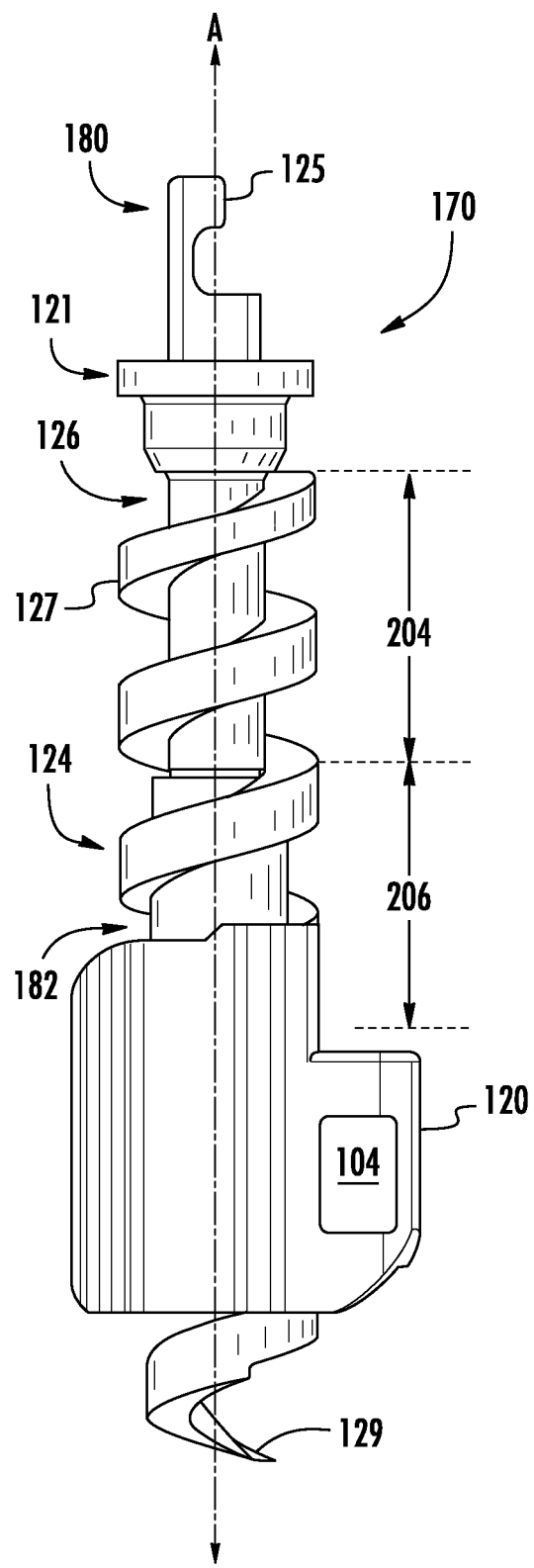
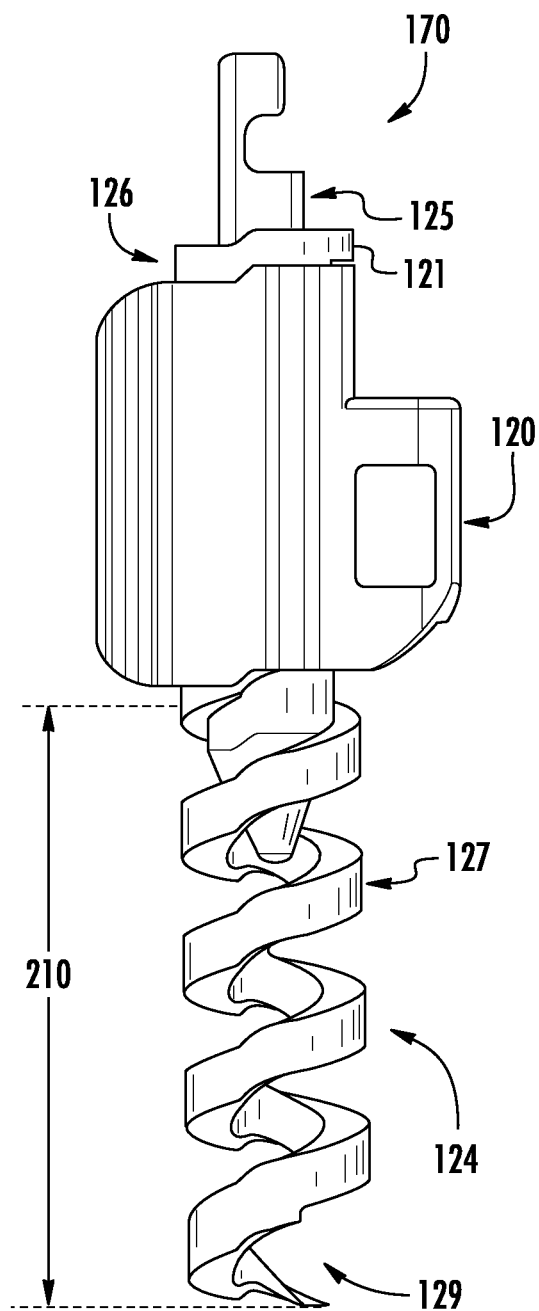
FIG. 2A
FIG. 2B

SPRING LOADED SELF LOCKING REVERSIBLE ANCHOR

CROSS-REFERENCE TO RELATED APPLICATIONS

The present application claims the benefit of priority under 35 U.S.C. § 119 to U.S. Provisional Patent Application 62/898,240, filed Sep. 10, 2019, which application is incorporated herein by reference in its entirety for all purposes.

FIELD

The present disclosure relates generally to the field of implantable medical devices. In particular, the present disclosure relates to medical devices, systems, and methods for annuloplasty and other cardiac treatment techniques.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques have been introduced that aim to restore a mitral valve to its native configuration, for example by implanting an annuloplasty ring around a valve annulus. One challenge encountered when deploying such implants arises due to the uneven topology of heart features, which may make it difficult to effectively anchor an implant. It is with these difficulties in mind that the disclosed solution is provided.

SUMMARY

According to one aspect, an anchor assembly includes an anchor including an anchor head and an anchor coil, the anchor coil including a proximal portion disposed about the anchor head and a distal portion extending distally from the anchor head. The anchor head may include a proximal end including a drive coupler, a distal tip, and an unthreaded shaft disposed between the drive coupler and the distal tip of the anchor head. The proximal portion of the anchor coil may include a compressible coil that is coupled to the distal tip of the anchor head.

In various embodiments, the anchor head may further include a flange disposed between the drive coupler and the unthreaded shaft of the anchor head, the flange configured to limit distal translation of the anchor through a bore of an anchor housing. The anchor head may include a locking feature, and the anchor housing may include a proximal slot configured to affix the locking feature to the anchor housing. The locking feature may include a flange, a tab, a tooth, a ridge, or some combination thereof, and the proximal slot may include a slot, a detent, a hole, a rail, or some combination thereof. In some embodiments, the flange may include the locking feature. Some embodiments may include an anchor housing having a bore extending therethrough, the bore including a threaded portion and an unthreaded portion, the threaded portion of the bore interacting with the anchor coil to provide axial translation of the anchor through the bore and the unthreaded portion of the bore interacting with the anchor coil to provide compression of the compressible coil.

According to another aspect, an annuloplasty system includes a delivery catheter including a drive tube having a proximal end and a distal end and an implant including an anchoring assembly. The anchoring assembly may include an anchor including an anchor head and an anchor coil including a compressible portion disposed for free movement about an unthreaded shaft of the anchor head, the compressible portion coupled at a distal end to a distal tip of the anchor head. The anchoring assembly may also include an anchor housing having a bore extending therethrough, the bore including a threaded portion and an unthreaded portion, the anchor coil interacting with the threaded portion of the bore to provide axial translation of the anchor through the bore and interacting with the unthreaded portion of the bore to provide compression of the compressible portion of the anchor coil.

In various embodiments, the anchor head may include a proximal drive coupler coupled to the distal end of the drive tube. The drive tube may be configured to provide a drive force, where the anchoring assembly converts the drive force from the drive tube to an axial translation force, a compression force, or both.

In one embodiment, the anchoring assembly may convert the drive force to the axial translation force when a proximal end of the compressible coil is within the threaded portion of the bore, and to the compression force when the proximal end of the compressible coil is within the unthreaded portion of the bore. The axial translation force may be configured to advance or remove the distal portion of the anchor coil from tissue, the compression force may be configured to draw together the anchoring assembly and the tissue, and the anchoring assembly may be configured to automatically convert the drive force from the axial translation force to the compression force in response to an interaction between the anchor head and the anchor housing.

In some embodiments, the compression force upon the compressible portion of the anchor coil may generate a tensile load on the compressible coil that draws together the anchor housing and the tissue. The anchor head may further include a flange disposed between the drive coupler and the unthreaded shaft of the anchor head, the flange configured to limit distal translation of the anchor through a bore of an anchor housing to convert the drive force to a compression force.

In some embodiments, the anchor head may include a locking feature, and the anchor housing may include a proximal slot configured to affix the locking feature to the anchor housing. The locking feature may include a flange, a tab, a tooth, a ridge, or some combination thereof, and the proximal slot may include a slot, a detent, a hole, a rail, or some combination thereof. In some embodiments, the flange includes the locking feature. In one embodiment, the drive tube may include a drive sheath that shrouds the locking feature of the anchor head to discourage engagement between the locking feature and the proximal slot of the anchor housing. The locking feature of the anchor head may be biased by the compression force to draw the locking feature into the proximal slot of the anchor housing when the drive sheath is withdrawn from the locking feature.

In one embodiment, the anchor may be one of a plurality of anchors of the implant, the anchor housing may be one of a plurality of anchor housings of the implant, and the drive tube may be one of a plurality of drive tubes of the delivery catheter, each of the plurality of drive tubes coupled to one of the plurality of anchors, where the drive tubes may be independently controlled to drive each anchor according to an anatomy of an anchoring location.

According to a further aspect, an annuloplasty method includes the step of deploying an implant system to a valve annulus, the implant including an anchor housing having a bore extending therethrough, an anchor, disposed within the bore of the anchor housing, an anchor head and an anchor coil including a compressible portion disposed about the anchor head and a tissue engaging portion distal from the compressible portion. The anchor coil may be attached to the anchor head at a distal tip of the anchor head. In one embodiment, a flange may be disposed at a proximal end of the anchor head, the flange configured to limit translation of the anchor through the bore of the anchor housing. The method includes the steps of driving the anchor through the bore of the anchor housing into tissue until the flange of the anchor limits distal translation of the anchor through the anchor housing and driving the anchor when distal translation of the anchor through the anchor housing is impeded to compress the compressible coil to draw together the anchor housing and the tissue.

In various embodiments, the anchor head includes a locking feature configured to engage a proximal slot of the anchor housing, and the step of continuing to drive the anchor when the distal translation of the anchor is impeded generates a tensile load in the anchor housing that biases the locking feature towards the proximal slot of the anchor housing.

With such an arrangement, a spring loaded anchoring assembly with improved anchor affixation and retention is provided.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 2A and 2B illustrate an example of an anchoring assembly as disclosed in various embodiments herein;

DETAILED DESCRIPTION

Figure 1:
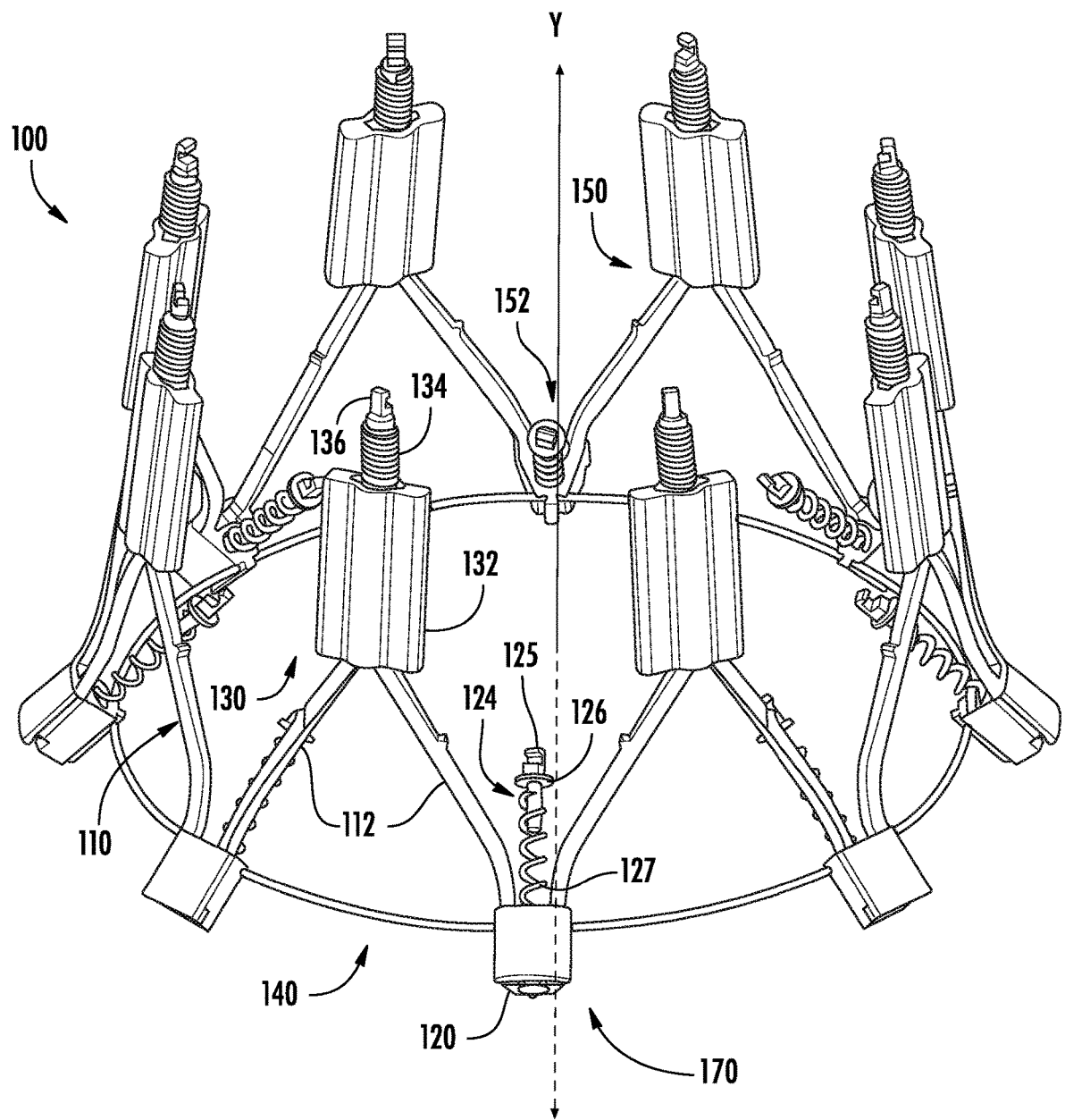
FIG. 1 is a diagram of one embodiment of an implant comprising anchoring assemblies as disclosed in various embodiments herein.

A spring loaded, self-locking anchoring assembly converts a drive force, administered to an anchor of the anchoring assembly, to one or both of an axial translation force or a compression force. The axial translation force may be used to drive the anchor into tissue, while the compression force may be used to further draw together anchor components and tissue, and/or to lock together anchor components, to improve anchor affixation in the presence of anatomical variations.

In one embodiment, an anchor of the anchoring assembly disclosed herein may include an anchor head coupled to an anchor coil. The anchor head may include a proximal flange, a distal tip, and an unthreaded shaft disposed between the proximal flange and the distal tip. The anchor coil may include a proximal, compressible portion, and a distal tissue engaging portion. The compressible portion may be fixedly attached at its distal end to the distal tip of the unthreaded shaft. The compressible portion of the anchor coil is otherwise disposed to move freely over the unthreaded shaft of the anchor head.

The anchor assembly also includes an anchor housing having a bore extending therethrough that is sized to support the anchor. In one embodiment, the bore includes a threaded portion and an unthreaded portion. The threaded portion of the bore interacts with the anchor coil of the anchor to translate drive forces administered to the anchor into axial translation forces to drive the tissue engaging portion of the anchor coil into tissue.

In one embodiment, the unthreaded portion of the bore cooperates with the unthreaded shaft of the anchor head when aligned within the anchor housing by distal translation of the anchor through the anchor housing. In one embodiment, the flange of the anchor head limits distal travel of the anchor through the anchor housing, aligning the unthreaded shaft of the anchor head with the unthreaded portion of the bore.

As described in more detail below, the unthreaded shaft of the anchor head may provide a so-called "free-spin" space, wherein in the free spin space, the anchor coil may be compressed to provide a tensile load. For example, further driving of the anchor when axial translation of the anchor is limited causes the compression portion of the anchor coil, which, as described, rides freely over the shaft, to continue to turn, entering the unthreaded portion of the bore. In this free-spin space, further activation of the driver increases the tensile load on the anchor coil which draws together the anchoring assembly and patient tissue to improve implant integrity. In one embodiment, cooperating features of the anchor and anchor housing may use the tensile load to lock the anchor to the anchor housing.

These and other beneficial aspects of an implant and method of deployment are described in more detail below. Although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage, and other similar heart failure conditions.

As used herein, the term "distal" refers to the end farthest away from the medical professional when introducing a medical device into a patient, while the term "proximal" refers to the end closest to the medical professional when introducing a medical device into a patient.

FIG. 1 illustrates an embodiment of an implant 100 that may include spring-loaded, self-locking anchor assemblies 170 such as those disclosed in various embodiments herein, including an anchor housing 120 and an anchor 124.

The implant is shown comprising a frame 110 that may be disposed about a heart valve or other cardiac feature. For purposes of clarity not all of the components of the implant are numbered. In one embodiment, the frame 110 may extend circumferentially around and partially axially along a central frame axis Y extending proximally-distally through a center point of the frame. The frame 110 may be generally symmetric with respect to the central frame axis although it need not be symmetric. The frame 110 may form a generally tubular shape, where herein "tubular" includes circular as well as other rounded or otherwise closed shapes. The frame 110 may be configured to change shape, size, and/or configuration. For example, the frame 110 may assume various shapes, sizes, configurations, etc. during different phases of deployment such as during pre-delivery, delivery, tissue engagement, and cinching.

According to one embodiment, the frame 110 may be formed from one or more struts 112 that may form all or part of the frame 110, where the struts 112 may include elongated structural members formed of a metal alloy, a shape memory material, such as an alloy of nickel titanium or other metals, metal alloys, plastics, polymers, composites, other suitable materials, or combinations thereof. In FIG. 1 sixteen struts 112 are shown although it is appreciated that in some embodiments, there may be fewer or more than sixteen struts.

In one embodiment, the struts 112 of the frame 110 may be formed from the same, monolithic piece of material (e.g. tube stock). Thus, reference to struts 112 may refer to different portions of the same, extensive component. Alternatively, reference to struts 112 may refer to components that are formed separately and attached permanently together, for example by welding or other methods. In some embodiments, the struts 112 may be separate components that are detachably coupled to form proximal apices 150 and distal apices 152. For example, the struts 112 are shown joined at their proximal apex by actuator 130 and at their distal apex by anchor housings 120.

In some embodiments, the terms "apex," apices," and the like may be used interchangeably with terms "crown," "crowns," and the like, as used herein and as used in any reference incorporated by reference herein, unless otherwise stated. In one embodiment, an 'apex' may include a proximal or distal portion of the frame.

In one embodiment, the actuator 130 includes an actuator shaft 134 that is rotatably carried by the proximal end of the frame 110. For example, a head of the actuator shaft 134 may be contained within an actuator collar 132 and be carried by a window or other opening (not shown) at the proximal apex 150 of the frame 110 to enable rotation of the shaft 134 within the actuator collar 132. The actuator shaft 134 may include a drive coupler 136 disposed at a proximal end.

The actuator collar 132 may include internal features configured to interact with the features of the actuator shaft 134 such that rotation of the actuator shaft 134 by an actuator drive tube coupled to the drive coupler 136 axially translates the actuator collar 132 over the actuator shaft 134 and over struts 112. In some embodiments, "axial" as applied to axial movement or restraint of the actuator collar includes those directions that are at least partially in the proximal or distal direction and that are parallel or generally parallel to a central axis extending through (e.g. proximally—distally) the frame. As shown in FIG. 1, struts 112 extend away from the proximal apex in opposing directions. Distal translation of the actuator collar 132 pulls struts 112 together within the actuator collar 132, thereby reducing the distance between anchor housings 120 for annular customization. Actuator collar 132 may be independently actuated in accordance with the reshaping objective for the associated anchor pair.

The anchor housings 120 are shown coupled by a cinch cord 140. Each anchor housing 120 carries an anchor 124 having an anchor head 126 coupled to an anchor coil 127. A drive coupler 125, disposed at the proximal end of anchor head 126 is configured to cooperate with a complementary feature of a drive tube (not shown) to axially translate the anchor 124 through the anchor housing 120 and into tissue. As described in more detail below, once the anchors 124 are driven through the anchor housings 120 and into tissue, features of the anchor head 126 inhibit further distal translation of the anchor 124 through the housing 120. At this point, as described in greater detail below, features of the anchor 124 cooperate with features of the anchor housings 120 to build a compression force within the anchor housing that operates to draw the anchor housing 120 together with tissue, for example annular tissue. The compression force may also be used to lock the anchor to the anchor housing.

For example, FIGS. 2A and 2B illustrate the anchor assembly 170 in more detail. FIG. 2A illustrates the anchor assembly 170 prior to anchor deployment into tissue. The anchor assembly 170 is shown to include an anchor 124 carried by an anchor housing 120. The anchor housing 120 may define a cinch lumen 104, for example for carrying the cinch lumen 140 (FIG. 1).

The anchor 124 includes an anchor head 126 having a proximal end 180 and a distal end 182. A drive coupler 125, disposed on the proximal end 180 of the anchor head, is configured to matingly engage with a driver (not shown) operable to translatably advance the anchor forward or backwards through anchor housing 120.

The anchor head 126 also includes a flange 121, coupled to or integral with the proximal end 180 of the anchor head 126. The flange 121 may comprise a collar, tab, or other feature that extends radially around or partially around a central axis A of the anchor head 126. In one embodiment, the flange 121 may limit the extent of distal travel of the anchor 124 through the anchor housing 120 when the flange 121 contacts the anchor housing 120 during distal travel of the anchor 124 through the anchor housing 120.

The anchor 124 may further comprise an anchor coil 127. In one embodiment, the anchor coil 127 comprises a proximal, compressible portion 204 configured to freely slide along the anchor head 126 in response to rotation of the anchor head 126.

The anchor coil 127 further includes a fixed portion 206, which is fixedly coupled to the anchor head 126. The anchor coil 207 further includes a distal, tissue engaging portion 129, where the tissue engaging portion 129 of the anchor coil 127 may be that portion of the anchor coil that extends distally from the fixed portion 206 of the anchor coil 127.

The anchor housing 120 includes a bore through which the anchor 124 translates during use. As will be described in more detail with regard to FIGS. 4A and 4B, in one embodiment, the bore of the anchor housing may include one or more features that interact with features of the anchor coil 127 to translate the anchor coil 127 through the anchor housing and/or to generate a compressive force to pull the anchor housing 120 towards tissue at a treatment site.

FIG. 2B illustrates one embodiment of an anchor assembly 170 wherein the anchor 124 has been translated through the anchor housing 120 by actuation of the drive coupler 125 until the flange 121 of the anchor head 126 contacts the anchor housing 120, impeding further distal travel of the anchor 124. The tissue engaging portion 129 of the anchor coil 127 is shown to extend to a maximum extent 210 beyond the anchor housing 120. The compressible portion of the anchor coil 127 (not shown in FIG. 2B) is disposed within the anchor housing 120 when the tissue engaging portion 129 has been advanced to its maximum distal extent 210.

Figure 3A:
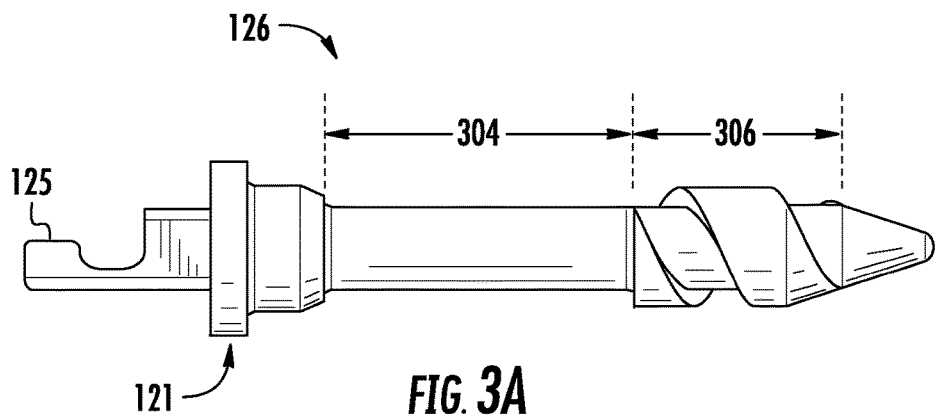
FIGS. 3A-3C illustrate components of the anchoring assembly of FIGS. 2A and 2B in more detail.
Figure 3B:
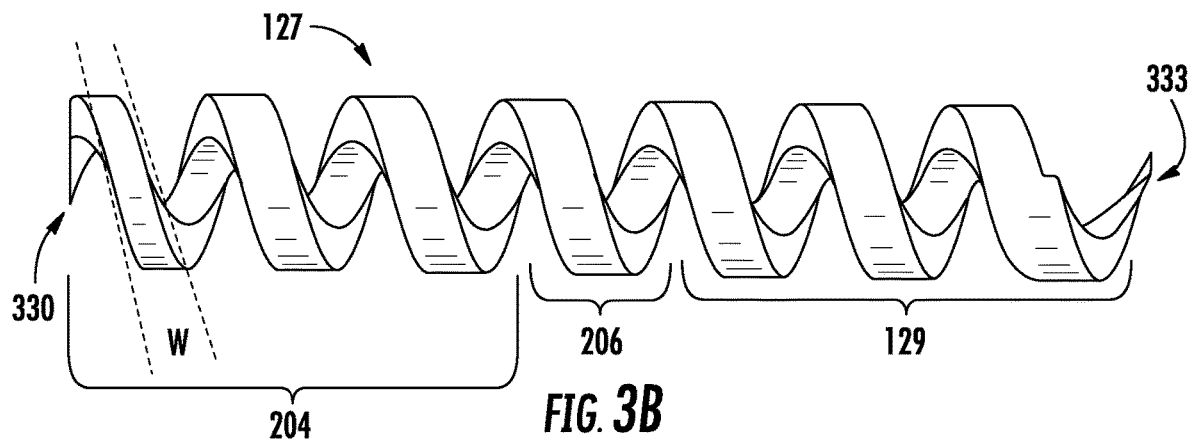
Figure 3C:
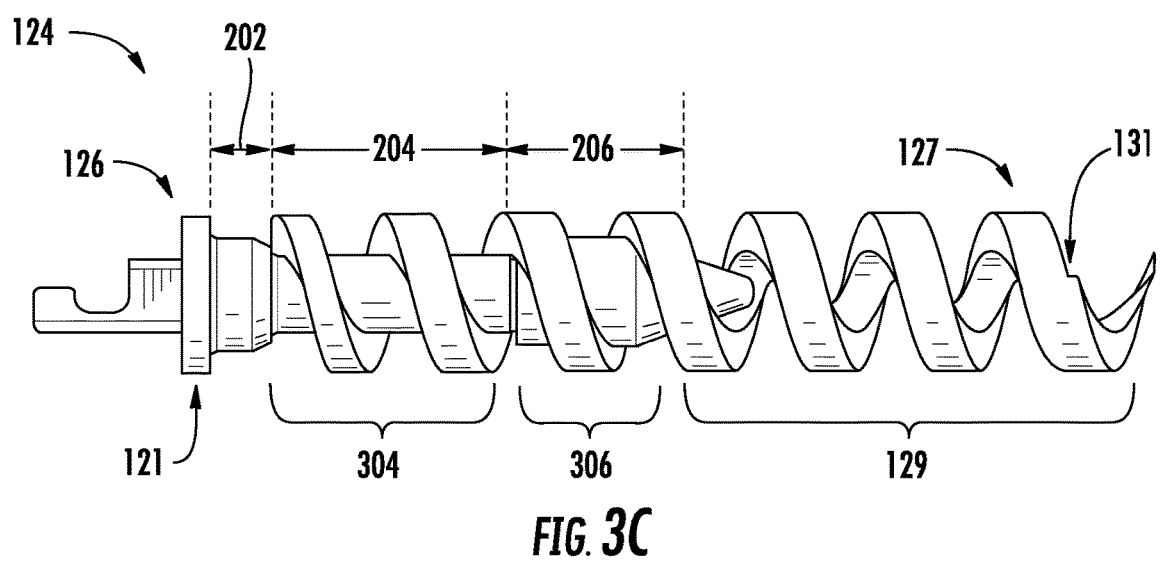

FIGS. 3A-3C illustrate embodiments of components of an anchoring assembly alone and in an assembled state. In FIG. 3A, the anchor head 126 is shown to include a generally hook shaped drive coupler 125 that is configured to cooperate with a complementary coupler of a drive tube (not shown) to drive the anchor of an implant. The anchor head 126 includes an unthreaded shaft 304 and a distal end 306. In one embodiment, the distal end 306 may be threaded to support complementary threads of an anchor coil, although the disclosure is not so limited. A flange 121 may be disposed between the unthreaded shaft 304 and the drive coupler 125. The flange 121 may include a tab, collar, or the like that extends radially from a central axis of the anchor head 126, to a diameter that exceeds a diameter of a bore of the anchor housing that supports the anchor.

In various embodiments, the length of the unthreaded portion 304 of the anchor head 126 may be selected to enable free spinning of the anchor within the anchor housing to pull together the anchor housing and tissue to accommodate for variations in tissue anatomy at a treatment area. For example, because an implant is seldom deployed on a flat surface, an implant may be disposed such that, when some apices contact a tissue surface, other apices of the implant are spaced apart from the tissue surface by different distances. Thus, different compression forces may be used to effectively pull together the tissue and the apices of the implant. The length of the unthreaded portion 304 is selected to accommodate the expected range of compressive forces for an implant. In some embodiments, the length of the unthreaded portion may comprise between 1-95% of the length of the anchor head. In some embodiments, the length of the unthreaded portion is greater than the length of the threaded portion of the bore (410, FIG. 4A). In some embodiments, the distal end 306 of the anchor head 126 comprises that portion that is affixed to a fixed portion 206 of the anchor coil 127 by welding or other means as shown in FIG. 3B.

FIG. 3B illustrates an example of an embodiment of an anchor coil 127, including a proximal end 330, a distal tip 333, a compressible portion 204, a fixed portion 206, and a tissue engaging portion 129. In some embodiments, the anchor coil 127 may be formed from a rounded wire. In other embodiments, the anchor coil 127 may be laser cut from a stainless steel hypo tube formed of full hard temper, type 304 stainless steel providing a helical anchor. In other embodiments, the anchor coil 127 may be cut from a stainless steel sheet and shaped to obtain the helical anchor configuration. In some embodiments, a thickness of the stainless steel sheet and/or hypo tube may range from between 0.020 mm to about 2 mm. In some embodiments, the thickness or width of the anchor coil may increase, decrease, and/or otherwise vary along the length of the anchor coil 127. For example, as shown in FIG. 3B, a width W of the anchor coil 127 tapers downward from the distal tips 333 to the proximal tip 330.

In some embodiments, the compressible portion 204 of the anchor coil 127 comprises between 1% and 30% of the anchor coil. In some embodiments, the compressible portion 204 comprises greater than 30% of the anchor coil. In some embodiments, the compressible portion 204 may include as little as a quarter turn of the anchor coil.

FIG. 3C illustrates the anchor 124 with the anchor head 126 and anchor coil 127 in an assembled state. The anchor coil 127 is coupled to the distal end 306 of the anchor head 126 at the fixed portion 206, and the compressible portion 204 forms a spring that rides freely along the unthreaded portion 304 of the anchor head 126.

In various embodiments the anchor 124 may be made of a suitable biocompatible metal alloy such as stainless steel, cobalt chromium, platinum iridium, nickel titanium, other suitable materials, or combinations thereof. Each anchor may be sharpened at its distal tip 333, or leading turn, so as to facilitate penetration into the cardiac tissue. In some embodiments, a barb 131 or other feature may be disposed at one or more location of the tissue engaging portion 129 of the anchor coil 127 to increase interaction between the anchor coil 127 and the tissue. Each anchor 124 may be from about ten to about fifteen millimeters (mm) in total axial length. In some embodiments, the anchors 124 may be shorter or longer than ten to fifteen millimeters (mm) in total axial length. By "total" axial length it is meant the axial length of the anchor 124 from the distal end of the anchor coil 127 to the opposite, proximal end of the anchor head 126. The anchor coil 127 may be from about six to about twenty millimeters (mm) in axial length. In some embodiments, the anchor coil 127 may be shorter or longer than six to twenty millimeters (mm) in axial length. The anchor head 126 and/or other non-helical portions of the anchor 124 may be from about three to about four millimeters (mm) in axial length. In some embodiments, the anchor head 126 and/or other non-helical portions may be shorter or longer than three to seven millimeters (mm) in axial length. In some embodiments, the distal end 129 may extend from about four to about ten millimeters (mm) into the cardiac tissue.

Figure 4A:
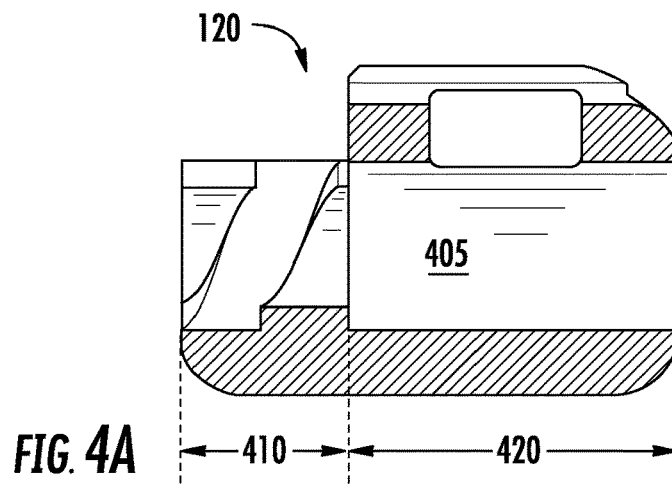
FIGS. 4A-4C are cross sectional views of one embodiment of the anchoring assemblies of FIGS. 2A and 2B.

FIG. 4A is a cross section diagram of anchor housing 120, in one embodiment. The anchor housing 120 is shown to comprise a bore 405 extending therethrough, the bore comprising a threaded portion 410 and an unthreaded portion 420.

Figure 4B:
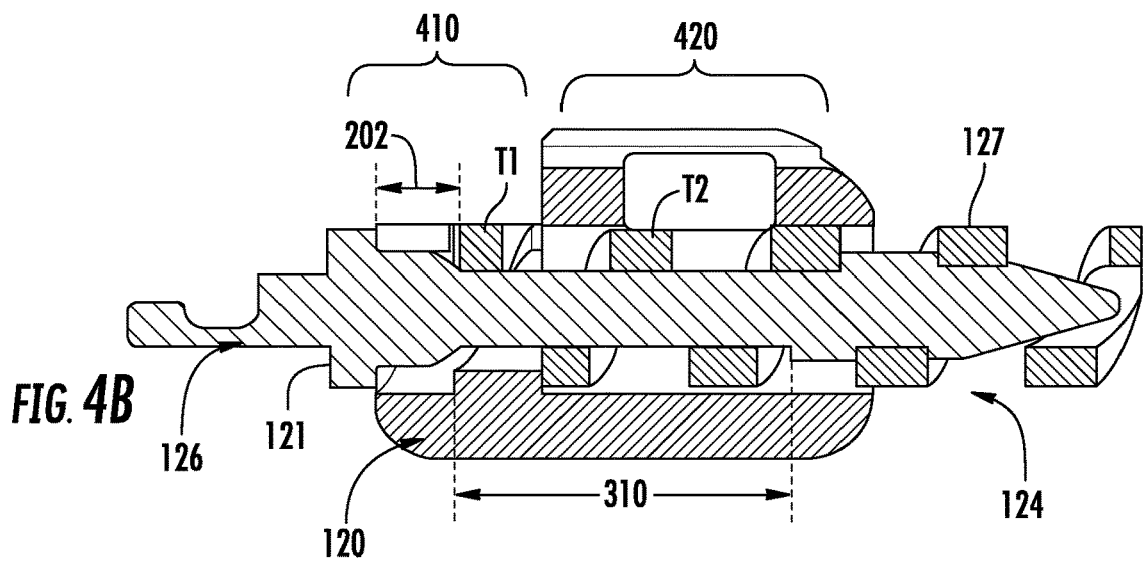

FIG. 4B is a cross section view of an anchor 124 disposed within the anchor housing 120. Turn T1 of anchor coil 127 is shown disposed within the threaded portion 410 of the bore of the anchor housing 120, while turn T2 is disposed within the unthreaded portion 420. The anchor 124 has been translated until the flange 121 contacts the anchor housing and displacement between the collar 121 and the proximal end of the anchor coil 127 is generally shown as 202. At this point, further force provided to the anchor 124 results in free spinning of the anchor, e.g. further rotation without axial translation. Because the proximal end of the anchor coil 127 is not attached to the anchor head, free spinning of the anchor pulls turn T1 into a compression cavity defined by the unthreaded portion of the bore, allowing the compression portion of the anchor coil 127 to move freely over the unthreaded portion 310 of the anchor head 126, increasing friction and tension within the anchor housing 120.

Figure 4C:
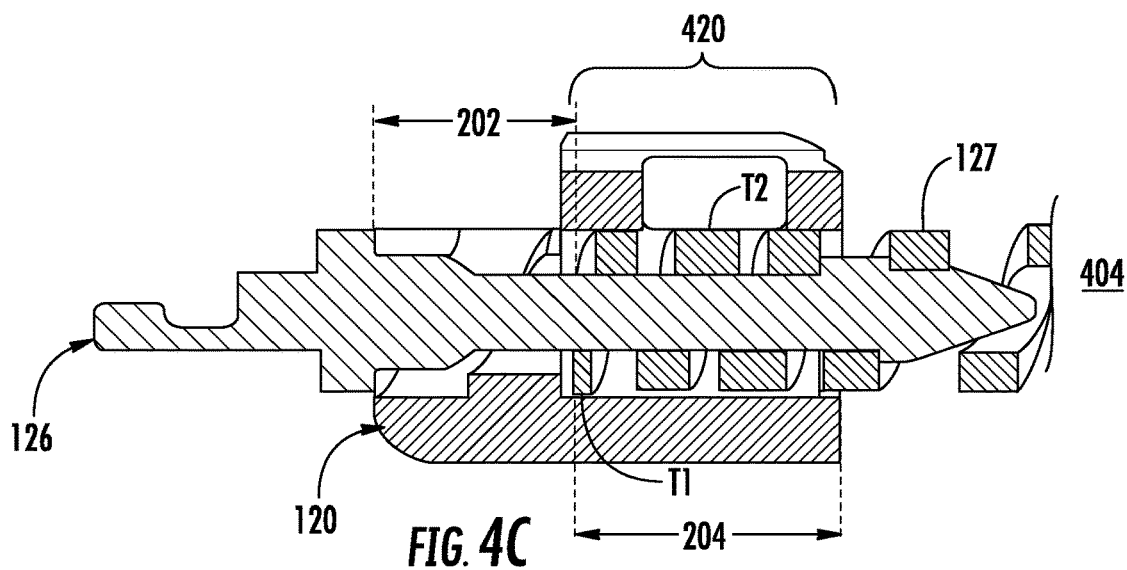

FIG. 4C illustrates compression of the compressible portion 204 of the anchor coil 127 during free spinning. Continued rotation of the anchor head 126 builds a tensile force within the bore, pulling turn T1 into the unthreaded portion 420 of the bore and increasing the displacement 202 between the proximal end of the anchor coil 127 and the flange 121. As a result, the tensile load on the anchor coil 127 increases and draws together the anchor housing 120 and tissue 404.

Accordingly, an anchor assembly has been shown and described that enables axial translation of anchors (forward and/or reverse) into heart features, for example to attach cardiac treatment components including but not limited to annuloplasty components. The anchor assemblies are configured to produce a spring-loaded compression force to pull together tissue and components to improve implant integrity and efficacy.

In addition, according to one embodiment, the compressive forces may further be used to securely join the anchor housing and anchor together, following anchor deployment, to reduce issues associated with anchor backout. In one embodiment, the anchor may include features that enable self-locking with the anchor housing using the compression load accumulated during free spinning of the anchor head. For example, the anchor may include a tab, slot or other feature that cooperates with a complementary slot, tab, or other feature of the housing to fixedly couple the anchor to the anchor housing. Locking the anchor to the anchor housing as described below inhibits further distal and/or proximal translation of the anchor within the anchor housing, effectively securing the anchor to the anchor housing. As a result, in the event that anchor should detach from tissue during chronic use, the lock feature fixedly retains the anchor within the anchor housing, eliminating the potential for the anchor to disengage from the implant and be released into the heart cavity.

Figure 5A:
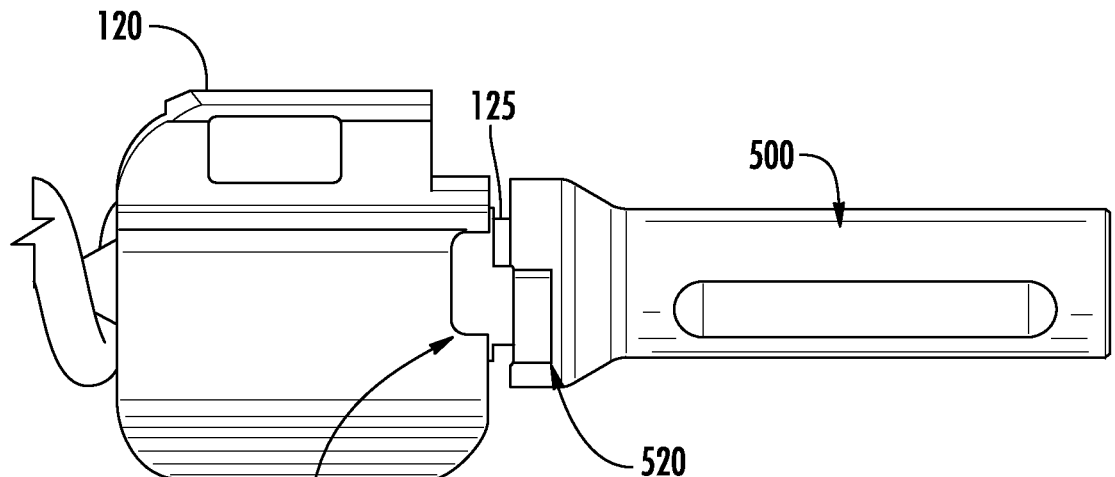
FIGS. 5A and 5B are perspective views of one embodiment of a lock feature of an anchoring assembly as disclosed herein.
Figure 5B:
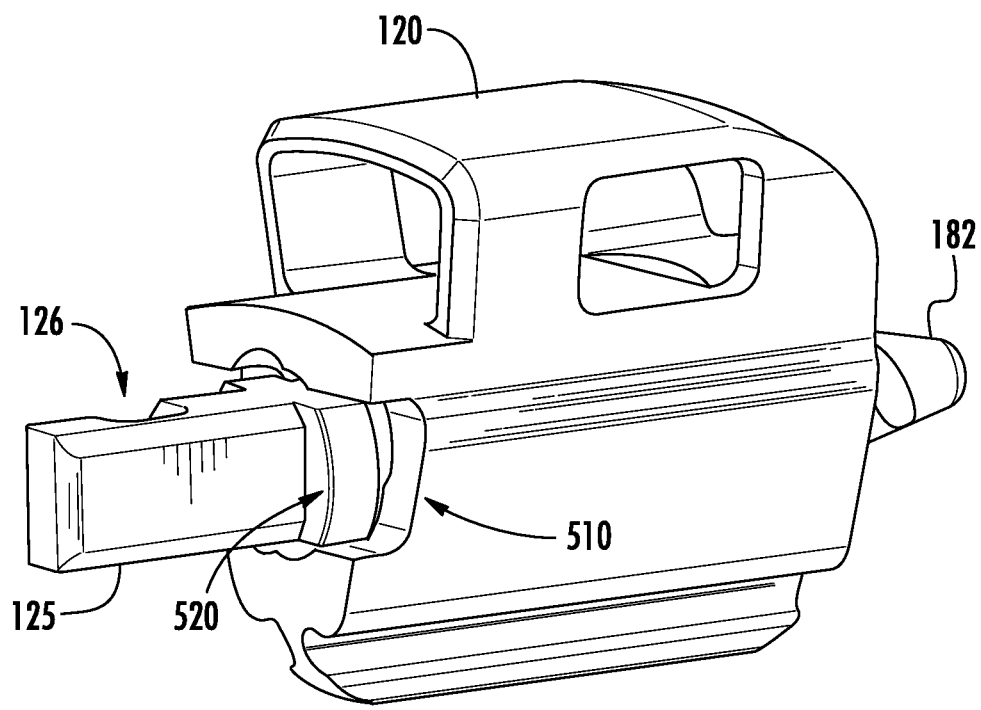

FIGS. 5A and 5B are perspective views of one embodiment of a lock feature of an anchor assembly as disclosed herein. In FIG. 5A, a portion of a deployment system is shown to include a drive sheath 500 disposed over the drive coupler 125 of the anchor head. The anchor head is shown to include a lock feature 520 which may include a flange, a tab, a nub, a protuberance or other feature which cooperates with a complementary feature 510, such as a slot, divot etc., of the anchor housing 120. In one embodiment, the lock feature 520 is shrouded by the drive sheath 500 while the drive sheath 500 is coupled to the drive coupler 125 of the anchor head. Shrouding the lock feature 520 using the drive sheath 500 advantageously prevents the lock feature 520 from engaging the complementary feature 510 on the anchor housing 120 during axial translation and free spinning of the anchor head by the driver.

Following affixation of the anchor to the tissue, including following further engagement of the tissue with the anchor housing 120 using free spinning to pull the housing and tissue together, the driver may be released from the drive coupler 125 as shown in FIG. 5B. To ease explanation, the anchor coil is omitted from FIG. 5B. As described above, during free spinning, a tensile load is generated within the anchor housing. Because the anchor coil is affixed to the distal end 182 of the anchor head, the tensile load urges the anchor head 126 distally. As a result, when the drive sheath is removed from the drive coupler 125, the lock mechanism is drawn down into the slot 510 of the housing, securing the anchor within the housing and minimizing potential for backout.

As mentioned above with regard to FIG. 1, the anchor assemblies described herein may benefit annuloplasty systems that deliver and affix components to heart features. Such annuloplasty systems generally include mechanisms for deploying implant components, including anchors, and for driving anchors as disclosed herein, including driving anchors to achieve axial translation and build compressive forces within anchor housings.

Figure 6A:
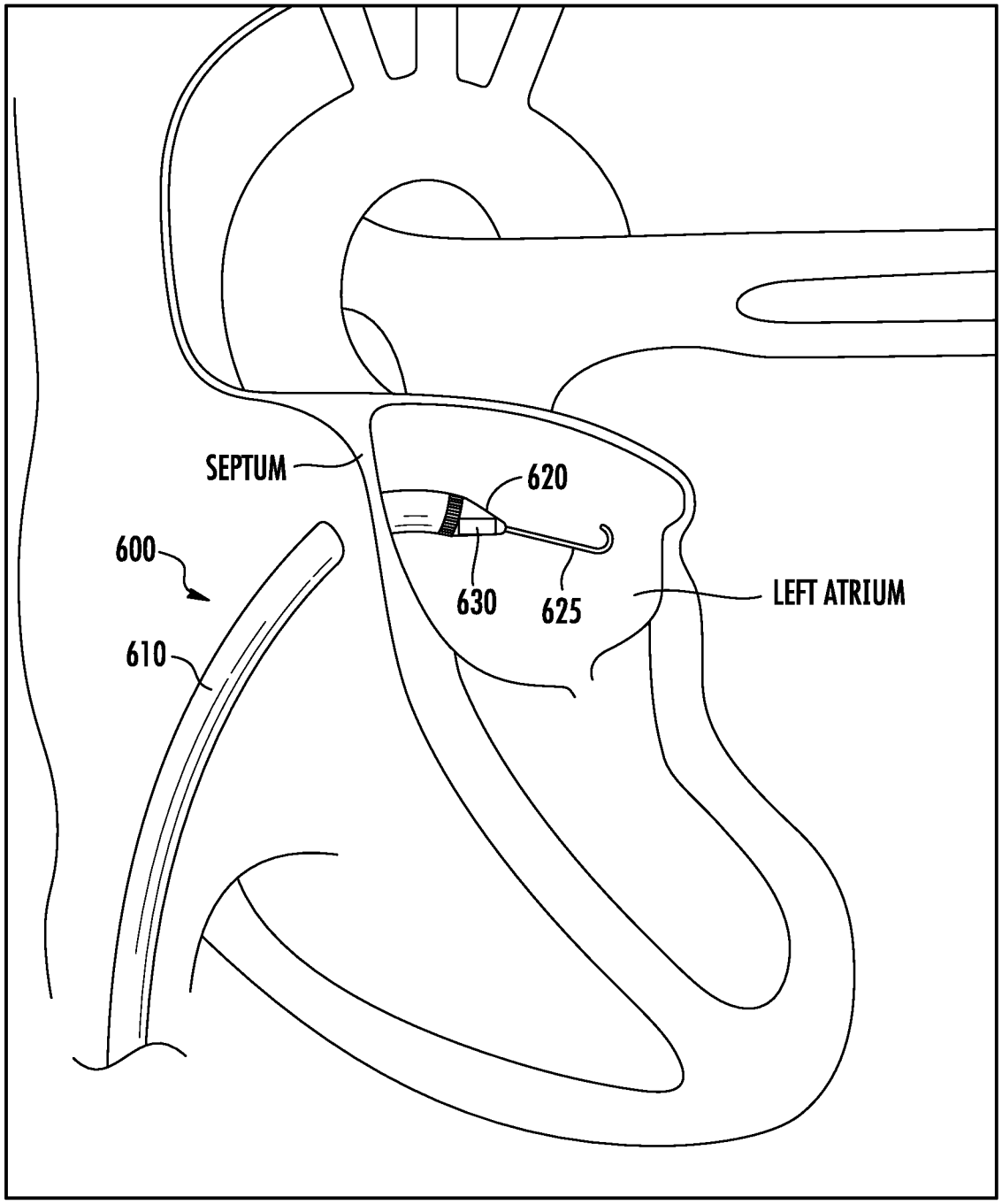
FIGS. 6A-6B illustrates an exemplary method for deploying an implant including anchoring assemblies as disclosed in various embodiments herein.
Figure 6B:
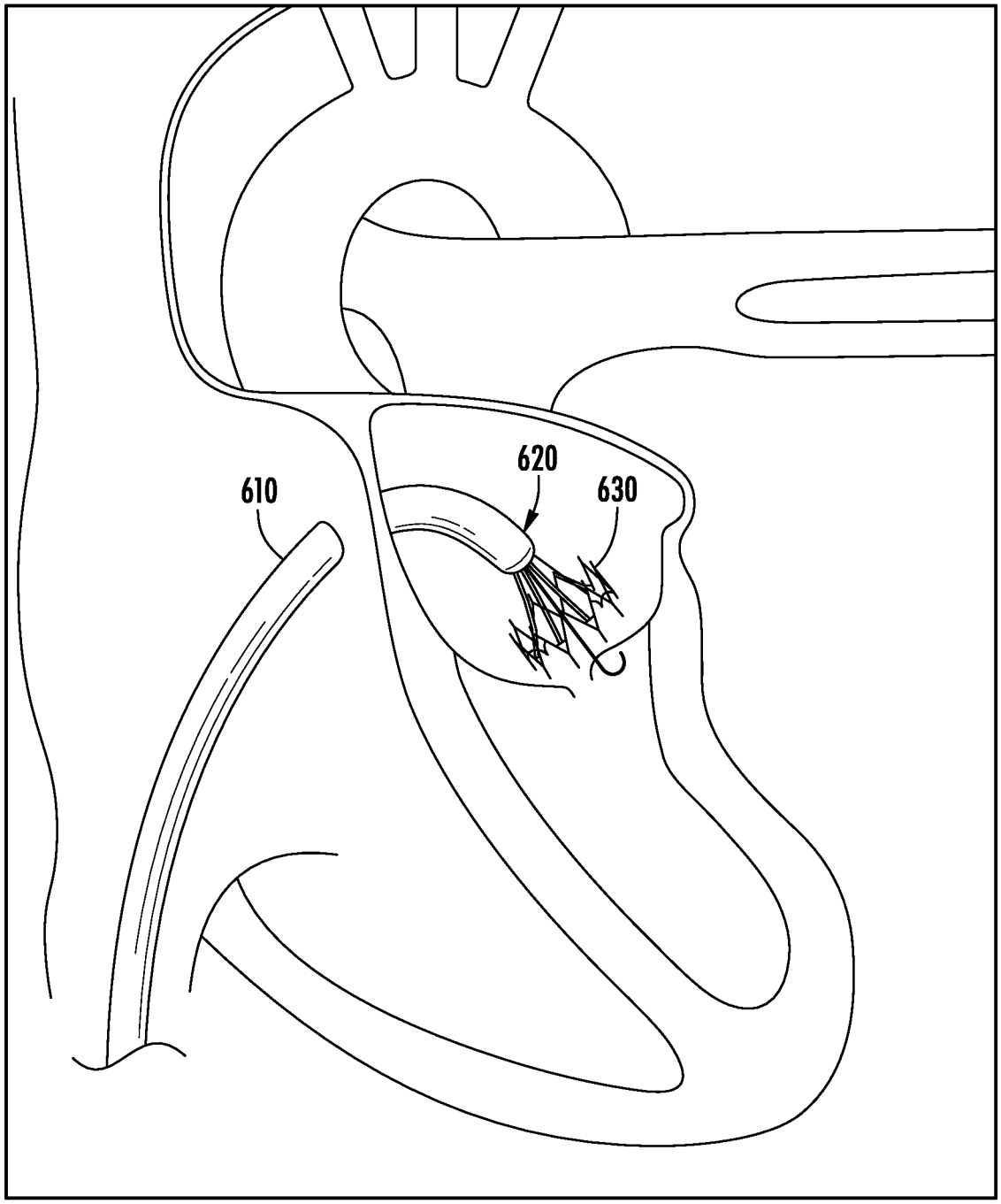

For example, referring now to FIGS. 6A and 6B, such an annuloplasty system 600 may include a deployment catheter 610 carrying annuloplasty components 630 at a distal end 620. The distal end of the deployment catheter 610 may be transluminally maneuvered into the left atrium, for example, to position the components above and/or around and/or partially around the mitral valve annulus using guidewire 625. According to one aspect, the deployment catheter may have various positioning and imaging capabilities, for example such as those described in U.S. patent Ser. No. 15/280,004 entitled "Methods for Deployment of Heart Valve Devices Using Intravascular Ultrasound Imaging", filed Sep. 29, 2016 and incorporated herein by reference.

Referring now to FIG. 6B, when the distal tip 620 of the deployment catheter 610 is appropriately positioned, the annuloplasty components 630 may be exposed (either by advancing the components 630 through the distal tip of deployment catheter 610 or by withdrawing the distal sheath over the components) and expanded to a tissue engaging diameter. Expansion may occur naturally, for example when the frame is formed of Nitinol or other shape memory or super elastic material that is biased towards an expanded state. In alternate embodiments, expansion may be mechanically controlled, for example through the use of a force applied within the frame using an inflatable balloon or the like. The systems and methods disclosed herein are not limited to any particular mechanism for positioning anchors for annular reconstruction, whether such positioning uses a ring or an expandable frame, and for example may use techniques described in U.S. Pat. No. 9,610,156 "Mitral Valve Inversion Prostheses" filed Dec. 24, 2014; U.S. Pat. No. 9,180,005 "Adjustable Endoluminal Mitral Valve Ring", filed Nov. 24, 2015; and U.S. patent application Ser. No. 15/352,288, entitled "Implantable Device And Deployment System For Reshaping a Heart Valve Annulus" filed Nov. 16, 2016, and issued as U.S. Pat. No. 10,555,813, each incorporated by reference herein in their entireties for all purposes.

Following deployment of the annuloplasty components to the heart valve, as described above the anchors may be axially translated through the anchor housings until further distal translation is impeded. Thereafter, the anchors may be driven to provide a compressive force to draw the anchor housing closer to tissue. Subsequently the drivers may be removed, with the compressive force locking the anchor to the anchor housing.

Figure 7:
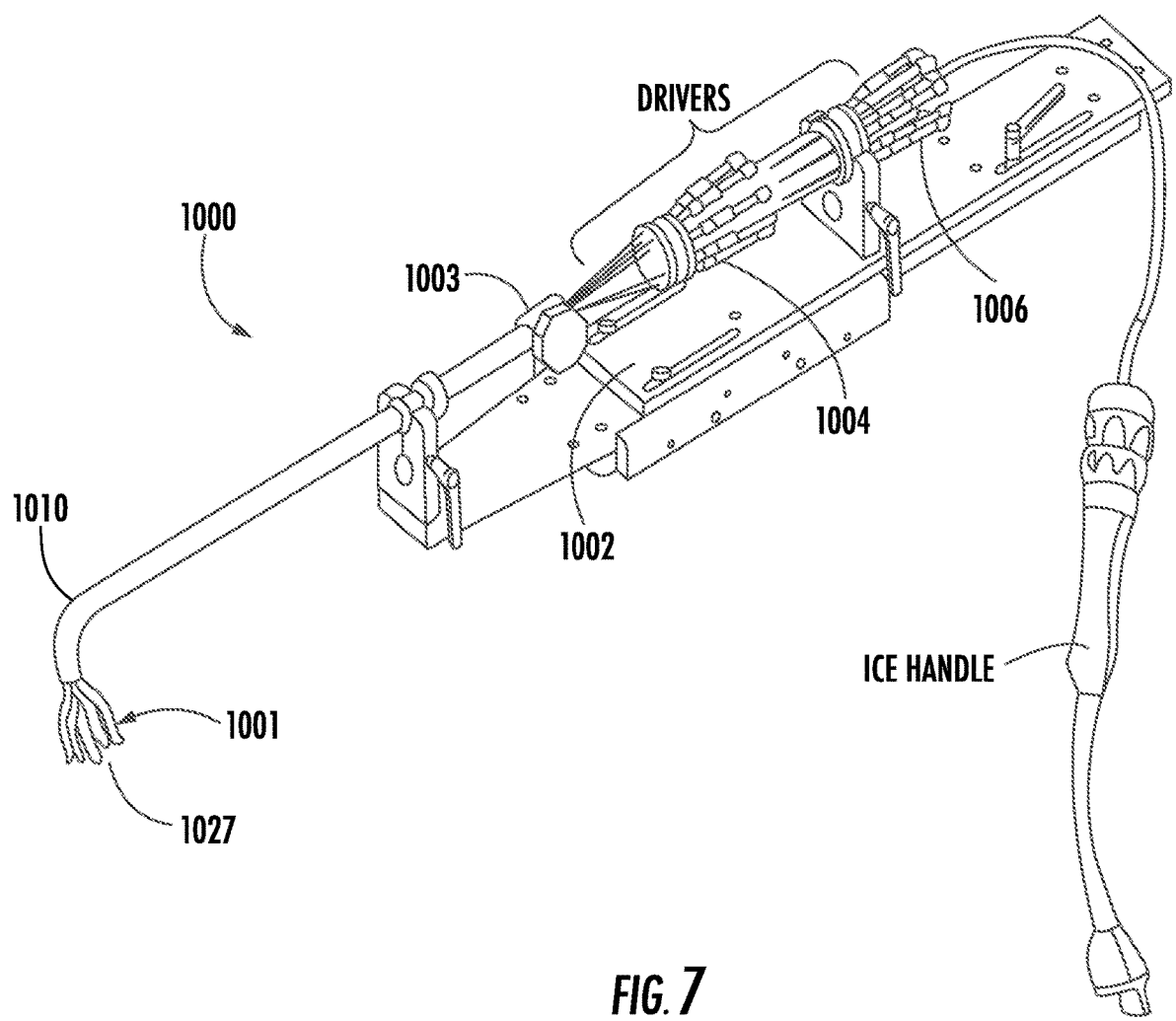
FIG. 7 illustrates an example of an embodiment of a control handle of an annuloplasty system that may be used to control placement and affixation of anchoring assemblies such as those disclosed herein.

FIG. 7 is a perspective view of an example of an embodiment of a deployment system 1000 that may be used to deploy an implant 1001 including anchoring assemblies such as those disclosed herein. The deployment system 1000 comprises a steerable sheath 1010, a sheath steering knob 1003, anchor knobs 1004, cinch knobs 1006, implant 1001, an Intra-Cardiac Echocardiography (ICE) probe 1027, all supported and secured to a base 1002. The cinch knobs 1006 and anchor knobs 1004 may be spring loaded to maintain tension. Rotation of the anchor knobs 1004 may rotationally advance the anchors into the anchor housings and further into annular tissue, to further drive the anchors when distal translation is impeded to draw together the tissue and anchors, and to release the anchors, allowing the compressive force to self-lock the anchor to the anchor housing.

Accordingly, various embodiments of spring-loaded, self-locking anchor assemblies have been shown and described. Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures that require anchoring to heart tissue. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment," "some embodiments," "other embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described herein, even if not explicitly shown in a particular combination, are nevertheless contemplated as being combinable or arrangeable with each other to form other additional embodiments or to complement and/or enrich the described embodiment(s), as would be understood by one of ordinary skill in the art.

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope, and concept of the disclosure as defined by the appended claims.

What is claimed is:

1. An anchor assembly comprising:
an anchor comprising an anchor head and an anchor coil; wherein:
the anchor coil comprises a proximal portion disposed about the anchor head and a distal portion extending distally from the anchor head;
the anchor head comprises a proximal end comprising a drive coupler, a distal tip and an unthreaded shaft disposed between the drive coupler and the distal tip of the anchor head; and
the proximal portion of the anchor coil comprises a compressible coil that is slidably coupled to the distal tip of the anchor head to allow compression of the compressible coil.

2. The anchor assembly of claim 1, wherein the anchor head further includes a flange disposed between the drive coupler and the unthreaded shaft of the anchor head, the flange configured to limit distal translation of the anchor through a bore of an anchor housing with respect to which the anchor head is mountable.

3. The anchor assembly of claim 2, wherein the anchor head includes a locking feature configured to be affixed to the anchor housing.

4. The anchor assembly of claim 3, wherein the locking feature includes a flange, a tab, a tooth, a ridge, or some combination thereof, and the proximal slot includes a slot, a detent, a hole, a rail, or a combination thereof.

5. The anchor assembly of claim 4, wherein the flange comprises the locking feature.

6. The anchor assembly of claim 3, comprising:
an anchor housing having a bore extending therethrough, the bore comprising a threaded portion and an unthreaded portion, the threaded portion of the bore interacting with the anchor coil to provide axial translation of the anchor through the bore and the unthreaded portion of the bore interacting with the anchor coil to provide compression of the compressible coil.

* * * * *